(12) United States Patent
Aarts

(10) Patent No.: US 10,721,890 B2
(45) Date of Patent: Jul. 28, 2020

(54) HYBRID CUCUMBER VARIETY 19-720 RZ

(71) Applicant: RIJK ZWAAN ZAADTEELT EN ZAADHANDEL B.V., De Lier (NL)

(72) Inventor: René Wilhelmus Adrianus Aarts, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 0 days.

(21) Appl. No.: 15/887,070

(22) Filed: Feb. 2, 2018

(65) Prior Publication Data

US 2018/0220615 A1 Aug. 9, 2018

Related U.S. Application Data

(60) Provisional application No. 62/454,986, filed on Feb. 6, 2017.

(51) Int. Cl.
*A01H 6/34* (2018.01)
*A01H 5/08* (2018.01)

(52) U.S. Cl.
CPC ............... *A01H 6/346* (2018.05); *A01H 5/08* (2013.01)

(58) Field of Classification Search
None
See application file for complete search history.

(56) References Cited

U.S. PATENT DOCUMENTS

| | | | |
|---|---|---|---|
| 8,445,753 B2* | 5/2013 | Torres | A01H 5/08 800/260 |
| 2014/0317769 A1* | 10/2014 | Suelmann | A01H 5/08 800/260 |
| 2014/0356514 A1* | 12/2014 | Suelmann | A01H 5/08 426/635 |
| 2015/0181824 A1* | 7/2015 | Suelmann | A01H 5/08 800/260 |
| 2015/0189845 A1* | 7/2015 | van der Maas | A01H 5/08 800/265 |
| 2017/0127631 A1* | 5/2017 | Shetty | A01H 5/08 |

* cited by examiner

*Primary Examiner* — Anne Kubelik
(74) *Attorney, Agent, or Firm* — Duane Morris LLP; Thomas J. Kowalski; Deborah L. Lu

(57) ABSTRACT

The present invention relates to a *Cucumis sativus* seed designated 19-720 RZ. The present invention also relates to a *Cucumis sativus* plant produced by growing the 19-720 RZ seed. The invention further relates to methods for producing the cucumber cultivar, represented by cucumber variety 19-720 RZ.

12 Claims, No Drawings

HYBRID CUCUMBER VARIETY 19-720 RZ

RELATED APPLICATIONS AND INCORPORATION BY REFERENCE

This application claims benefit of and priority to U.S. provisional patent application Ser. No. 62/454,986 filed Feb. 6, 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new hybrid cucumber (*Cucumis sativus*) variety designated 19-720 RZ.

BACKGROUND OF THE INVENTION

Cucumber plants of the species *Cucumis sativus* belong to the cucurbit family, scientifically called the Cucurbitaceae. Within this family it belongs to the genus *Cucumis*, which does not only contain the important food crop cucumber, *Cucumis sativus*, but also a variety of melon types mainly included in *Cucumis melo*, as well as several other, less well-known species. It is an annual, herbaceous, flowering plant species which is thought to have originated in Asia.

Cucumber plants were domesticated early and have been cultivated for thousands of years in African and Asian countries. A wild progenitor of cucumber is found in Asia and taxonomically classified as a subspecies, *Cucumis sativus* ssp. *hardwickii*. The closest related other species within the genus is acknowledged to be *Cucumis hystrix*. Small *Cucumis sativus* types are used for pickling and are called gherkins or pickling cucumbers. However, varieties of *Cucumis anguria* are also small fruited and can be grown for the same purpose; they are usually called 'bur cucumber' or 'West Indian cucumber'.

Cucumbers are presently cultivated worldwide in a large variety of types, which typically differ in size, color, and skin type. Cucumber fruits have a high water content and are therefore low in calories, but provide a source of various useful nutrients such as potassium, magnesium, calcium, and phosphorus, as well as vitamin C.

In 2012, the total acreage for fresh market cucumbers in the United States was approximately 19,150 hectares, with a total production of about 453 metric tons, representing a value of almost $248 million. Processing cucumbers or gherkins for pickles were harvested from 35,760 hectares which resulted in a production of about 448 metric tons, having a value of close to $172 million (source: USDA Vegetables 2012 Summary).

Cucumber production is most successful in a relatively warm climate and it prefers temperatures between about 18-25° C. Several pests and diseases can affect cucumber production, including several viruses that are often transferred by insects, but also bacterial and fungal diseases. Typical problems that might arise during cucumber production include downy mildew (*Pseudoperonospora cubensis*); powdery mildew (*Golovinomyces cichoracearum* and *Podosphaera xanthii*); Anthracnose (*Colletotrichum orbiculare*); Scab (*Cladosporium cucumerinum*); Angular leaf spot (*Pseudomonas syringae pv. lachrymans*); Belly rot (*Rhizoctonia solani*); Pythium fruit rot (*Pythium* spp.); the viruses Watermelon Mosaic Virus (WMV), Cucumber Vein Yellowing Virus (CVYV), Cucumber Mosaic Virus (CMV), Papaya Ringspot Virus (PRSV), Zucchini Yellow Mosaic Virus (ZYMV), Cucumber Green Mottle Mosaic Virus (CGMMV); and pest attacks by aphids, cucumber beetles, spider mites, and pickleworms.

Breeding for resistance against any of the diseases and pests that are mentioned above, or any other biotic or abiotic stress factors, is an important aspect in providing varieties for multiple growing systems and climates. It is preferred to breed for a combination of resistances to create a variety that is most suitable in a certain situation or environment.

In order to create cucumber varieties that are satisfying the needs of growers and/or consumers, many considerations have to be taken into account. The goal in a breeding program is to combine within a single variety or hybrid an improved combination of desirable traits from the parental germplasm. These traits may include higher yield, field performance, resistance to diseases and insects, and tolerance to drought, cold and heat. Like for most fruit crops, also for cucumber it is apparent that fruit quality is of the utmost importance. Fruit quality includes aspects such as external and internal color, shelf life, fruit size, skin type, firmness, texture, and size of the seed cavity. In addition, characteristics related to optimum plant development are very important for the grower, such as uniformity and speed of germination, growth rate, time to maturity, and plant uniformity. Since many hybrid varieties are gynoecious, bearing only female flowers, the capacity for parthenocarpic fruit set is then also an essential trait.

Cucumber is a diploid plant species with seven pairs of chromosomes. Cultivated cucumber plants have male and female flowers, which can be present together in monoecious plants, but in present-day cultivars commonly gynoecious (all female) plants are used. Cucumbers are easy cross-pollinators but can also self-pollinate when female and male flowers are present in the same plant.

Like in most crops, commercial cucumber cultivars were initially open-pollinated, but nowadays many high yielding hybrid varieties are available, often parthenocarpic. Cucumbers are grown throughout the world, mainly in open field, and are adapted to many different climates and circumstances. As mentioned earlier, many different types are available, and different regions have different preferences in size, fruit type, skin color, etc. Since most cucumber types belong to the same species, limited crossing barriers exist and combinations between types are frequently developed in breeding programs, although certain specific characteristics might be difficult to recombine into a new type.

Early flowering plants that have a good fruit set contribute largely to the potential yield of a pickling crop. Gynoecious flowering in combination with the ability to parthenocarpic fruit set without a large number of aborting fruits provides the growers with the option to use the acreage efficiently. No space is required for plants that have to be used to provide the pollen, and the presence of pollinating insects does not influence the setting of parthenocarpic fruits. A fruit size and type that are fitting the growers' needs plays an important role in choosing a suitable variety.

Growers rely on the presence of resistances to pests and diseases in anticipation of a good cucumber crop. In addition, the presence of resistances requires lower pesticide inputs, which benefits both the expenses for the farmer and the environment.

Citation or identification of any document in this application is not an admission that such document is available as prior art to the present invention.

SUMMARY OF THE INVENTION

The present invention provides a new cucumber (*Cucumis sativus*) variety, designated 19-720 RZ.

The present invention provides seeds of cucumber cultivar 19-720 RZ, which have been deposited with the National Collections of Industrial, Marine and Food Bacteria (NCIMB) in Bucksburn, Aberdeen AB21 9YA, Scotland, UK and have been assigned NCIMB Accession No. 42966.

In one embodiment, the invention provides a cucumber plant designated 19-720 RZ, representative seed of which have been deposited under NCIMB Accession No. 42966.

In one embodiment, the invention provides a cucumber plant designated 19-720 RZ, as well as seed from such a plant, plant parts of such a plant (such as those mentioned herein) and plants from such seed and/or progeny of such a plant, advantageously progeny exhibiting the same morphological and physiological characteristics as such a plant, each of which is within the scope of the invention.

In one embodiment the invention relates to a cucumber plant that has genetic material for exhibiting all of the morphological and physiological characteristics of a plant of the invention. The genetic information for exhibiting all of the morphological and physiological characteristics is as contained in a plant, representative seed of which having been deposited under NCIMB Accession No. 42966.

In an embodiment of the present invention, there also is provided a part of a cucumber plant of the invention, including a part of hybrid cucumber variety 19-720 RZ, wherein the plant part is involved in sexual reproduction, which includes, without limitation, a microspore, pollen, an ovary, an ovule, an embryo sac or an egg cell and/or wherein the plant part is suitable for vegetative reproduction, which includes, without limitation, a cutting, a root, a stem, a cell, or a protoplast and/or wherein the plant part is a tissue culture of regenerable cells in which the cells or protoplasts of the tissue culture are derived from a tissue such as, for example and without limitation, a leaf, pollen, an embryo, a cotyledon, a hypocotyl, a meristematic cell, a root, a root tip, an anther, a flower, a seed or a stem. The plant of the invention from which such a part may come includes those wherein representative seed has been deposited under NCIMB Accession No. 42966.

In another embodiment there is a plant grown from a seed, representative seed of which having been deposited under NCIMB Accession No. 42966. In a further embodiment there is a plant regenerated from an above-described plant part, or regenerated from the above-described tissue culture. Advantageously such a plant may have morphological and/or physiological characteristics of hybrid cucumber variety 19-720 RZ and/or of a plant grown from seed, representative seed of which having been deposited under NCIMB Accession No. NCIMB 42966—including without limitation such plants having all of the morphological and physiological characteristics of hybrid cucumber variety 19-720 RZ and/or of a plant grown from seed, representative seed of which having been deposited under NCIMB Accession No. NCIMB 42966. Accordingly, in still a further embodiment, there is provided a cucumber plant having all of the morphological and physiological characteristics of hybrid cucumber variety 19-720 RZ, representative seed of which having been deposited under NCIMB Accession No. 42966. Such a plant may be grown from a seed, regenerated from an above-described plant part, or regenerated from the above-described tissue culture. A cucumber plant having all of the resistances and the characteristics recited and tabulated herein is preferred. Parts of such a plant—such as those plant parts above-mentioned—are encompassed by the invention.

In one embodiment, there is provided progeny of cucumber cultivar 19-720 RZ produced by sexual or vegetative reproduction, grown from a seed, regenerated from an above-described plant part, or regenerated from the above-described tissue culture of the cucumber cultivar or a progeny plant thereof, representative seed of which having been deposited under NCIMB Accession No. 42966.

Progeny of the hybrid cucumber variety 19-720 RZ may be modified in one or more other characteristics, in which the modification is a result of, for example and without limitation, mutagenesis or transformation with a transgene.

In still another embodiment, the present invention provides progeny of cucumber cultivar 19-720 RZ produced by sexual or vegetative reproduction, grown from a seed, regenerated from an above-described plant part, or regenerated from the above-described tissue culture of the cucumber cultivar or a progeny plant thereof.

In one embodiment the invention relates to progeny of a cucumber plant, wherein the progeny has genetic material which is as contained in a plant, representative seed of which having been deposited under NCIMB Accession No. 42966.

In another embodiment the invention relates to a method of producing an inbred cucumber plant derived from a plant of the invention of which representative seed has been deposited under NCIMB Accession No. NCIMB 42966, which may comprise of the steps: a) preparing a progeny plant derived from hybrid cucumber variety 19-720 RZ by crossing a cucumber plant designated 19-720, representative seed of which have been deposited under NCIMB Accession No. 42966 with a second cucumber plant; b) crossing the progeny plant with itself or a second cucumber plant to produce a seed of a progeny plant of a subsequent generation; c) growing a progeny plant of a subsequent generation from said seed and crossing the progeny plant of a subsequent generation with itself or a second cucumber plant; and d) repeating step b) or c) for at least 1 more generation to produce an inbred cucumber plant derived from the hybrid cucumber variety 19-720 RZ. The invention further encompasses an inbred plant produced by such method.

The invention even further relates to a method of producing cucumber fruits which may comprise: (a) cultivating the hybrid cucumber variety 19-720 RZ, representative seed of which having been deposited under NCIMB Accession No. NCIMB 42966, to produce fruits and; (b) harvesting cucumber fruits from the plant. The invention further comprehends the fruit itself, optionally as part of a food product, optionally in processed or packed form.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

Deposit

The Deposit with NCIMB Ltd, Ferguson Building, Craibstone Estate, Bucksburn, Aberdeen AB21 9YA, UK, on Feb. 1, 2018, under deposit accession number NCIMB 42966 was made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention provides methods and compositions relating to plants, seeds and derivatives of a new hybrid cucumber variety herein referred to as hybrid cucumber variety 19-720 RZ. 19-720 RZ is a hybrid plant variety that is uniform and distinct from other such hybrids, and may be stably produced after a cycle of reproduction. Cucumber 19-720 RZ is a cucumber type that is ideal as a snack because of its small size, and is also known under designation Quatrino RZ F1.

There are numerous steps in the development of any novel plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant or plants. These important traits may include but are not limited to higher yield, field performance, fruit and agronomic quality such as fruit shape, size, and color, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes coding for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial cucumber hybrids relates to the development of cucumber parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Pedigree breeding is used commonly for the improvement and development of inbred lines of self-pollinating or cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, generally the best individuals in the best families are selected. Replicated testing of families, or hybrid combinations involving individuals of these families, often follows in the F4 generation to improve the effectiveness of selection for traits with low heritability. At an advanced stage of inbreeding suitable lines are used as parents to produce F1 hybrids, which are subsequently tested for potential release as new varieties or cultivars.

Mass and recurrent selections may be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g. the cultivar or parent line) and the desirable trait transferred from the donor parent. After the initial cross, individuals possessing the phenotype of the donor parent for the preferred trait are selected and repeatedly crossed (backcrossed) to the recurrent parent. The resulting plant is expected to have the attributes of the recurrent parent (e.g. the cultivar or parent line) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant may also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs). Nowadays, sequence-based methods are utilizing SNPs that are randomly distributed across genomes as a common tool for genotyping (e.g. Elshire et al. PloS One Vol. 6: e19379, 2011; Poland et al. PloS One Vol. 7: e32253; Truong et al. PloS One Vol. 7 number 5: e37565, 2012).

With any of the aforementioned genotyping techniques, polymorphisms may be detected when the genotype and/or sequence of the plant of interest is compared to the genotype and/or sequence of one or more reference plants. As used herein, the genotype and/or sequence of a reference plant may be derived from, but is not limited to, any one of the following: parental lines, closely related plant varieties or species, complete genome sequence of a related plant variety or species, or the de novo assembled genome sequence of one or more related plant varieties or species.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers may also be used during the breeding process for the selection of qualitative traits. For example, markers closely linked to alleles or markers containing sequences within the actual alleles of interest may be used to select plants that contain the alleles of interest during a backcrossing breeding program. The markers may also be used to select toward the genome of the recurrent parent and against the markers of the donor parent. This procedure attempts to minimize the amount of genome from the donor parent that remains in the selected plants. It may also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into cucumber varieties. Mutations that occur spontaneously or are artificially induced may be useful sources of variability for a plant breeder. The goal of artificial mutagenesis is to increase the rate of mutation for a desired characteristic. Mutation rates may be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding may be found in Principles of Cultivar Development by Fehr, Macmillan Publishing Company, 1993.

The production of doubled haploids may also be used for the development of homozygous lines in a breeding program. Doubled haploids are produced by the doubling of one set of chromosomes from a heterozygous plant to produce a completely homozygous individual. For example, see Wan et al., Theor. Appl. Genet., 77:889-892, 1989

The cucumber plant of the invention may be arrived at through crossing of inbred lines or through selection of the disclosed desirable characteristics by any of the breeding and selection methods mentioned above.

Hybrid snack cucumber variety 19-720 RZ is a cross between two uniform parent lines. The female line is a double haploid-line (DH) obtained from a cross between a variety from Central Asia that has a well filled fruit and short fruit length, and a North West European mini cucumber. The female line was selected for the trait small leaf, powdery mildew resistance, and CMV intermediate resistance. The male line is also a double haploid-line (DH) obtained from a cross between an Asian variety and a mini cucumber line out of the internal RZ program. It was selected for the traits dark stem, small leaf, and powdery mildew high resistance. The hybrid was developed in 2012 and tested since 2013 in the Netherlands, Japan, Turkey, Spain, and Canada.

In one embodiment, a plant of the invention has all the morphological and physiological characteristics of cucumber variety 19-720 RZ. These characteristics of a cucumber plant of the invention, e.g. variety 19-720 RZ, are summarized in Table 1. In Table 2 the main differences with a comparable publicly available variety are given, when grown under the same conditions.

The information presented in Tables 1 and 2 was determined in trial experiments in accordance with official Dutch plant variety registration authorities (Naktuinbouw).

The terminology and descriptors used by the Naktuinbouw, and accordingly in Table 1, are in line with the descriptors of the "UPOV Guidelines for the Conduct of Tests for Distinctness, Uniformity, and Stability", or the "Test Guidelines" for *Cucumis sativus*. The "Test Guidelines" indicate reference varieties for the descriptors or characteristics that are included in the list. Test guidelines for all crops may be accessed through the UPOV website, at http://www.upov.int/test_guidelines/en/index.jsp. For cucumber and gherkin, the most recent English Test Guideline TG/61/7, including reference varieties, was updated in 2014 and 2015, and is accessible at http://www.upov.int/edocs/tgdocs/en/tg061.pdf. The terminology and descriptors used in these tables are in line with the official terminology as of the filing date, and are thus clear for a person skilled in the art.

In addition the "Calibration book of *Cucumis sativus* L.—Cucumber" (Version 1, NAKTuinbouw, 2010) provides even more detailed reference information on most of the characteristics that are included in Table 1.

As used herein resistances against *Cladosporium cucumerinum* (Ccu), *Cucumis* Mosaic Virus (CMV), powdery mildew *Podosphaera xanthii* (Px), downy mildew *Pseudoperonospora cubensis* (Pcu), *Corynespora cassiicola* (Cca), Cucumber Vein Yellowing Virus (CVYV), and Zucchini yellow mosaic virus (ZYMV) are determined in accordance with the protocol as described in the UPOV "Test Guidelines" TG/61/7 for *Cucumis sativus*.

As used herein, 'stem: intensity of green color' relates to the color of the stem at seedling stage. The comparison variety Quarto RZ has a normal green color, while 19-720 RZ has a dark green stem color in seedling stage, which is a trait that is described and claimed in the published US patent application Ser. No. 14/841,880. Further, in relation to this trait, the intensity of the green color of the skin of the fruit of 19-720 RZ is 'Dark to very dark'.

TABLE 1

Physiological and morphological characteristics of hybrid cucumber variety 19-720 RZ
Variety description information for 19-720 RZ

| General: | |
|---|---|
| Method of maintenance and reproduction of the variety: | hybrid Seed propagated |
| Main use: | Fresh market |
| Fruit type | Cocktail/Beth Alpha |
| Type of culture: | Greenhouse, staked |
| Seedling: | |
| Cotyledon - bitterness: | absent |
| Plant: | |
| Leaf blade - length: | Very short |
| Leaf blade - intensity of green color: | Dark to very dark |
| Time of development of female flowers (80% of plants w/ at least 1 female flower): | medium |
| Sex expression: | gynoecious |
| Number of female flowers per node: | Predominantly more than five |
| Young fruit: | |
| Ovary - color of vestiture: | white |
| Fruit: | |
| Parthenocarpy: | present |
| Length: | very short to short |
| cm: | 6-8 cm |
| Shape of stem end: | Obtuse |
| Ground color of skin at market stage: | Green |
| Intensity of ground color of skin at market stage: | Dark to very dark |
| Creasing: | absent |
| Degree of creasing: | Not applicable |
| Type of vestiture: | Prickles only |
| Length of stripes: | Absent or very short |
| Dots: | absent |
| Disease and pest resistances: | |
| Cucumber mosaic virus (CMV): | resistant (IR) |
| Cucumber Vein Yellowing Virus (CVYV): | susceptible |
| Papaya Ringspot Potyvirus (PRSV): | Not tested |

TABLE 1-continued

Physiological and morphological characteristics of hybrid cucumber variety 19-720 RZ
Variety description information for 19-720 RZ

| | |
|---|---|
| Watermelon Mosaic Virus (WMV): | Not tested |
| Zucchini Yellow Mosaic Virus (ZYMV): | susceptible |
| Cucumber Green Mottle Mosaic Virus (CGMMV): | Not tested |
| *Pseudomonas syringae* pv lachrymans (Psl): | Not tested |
| *Corynespora cassiicola*/melonis (Cca): | susceptible |
| *Cladosporium cucumerinum* (Ccu): | Resistant |
| *Fusarium oxysporum* f. sp. *radicis-cucumerinum* (For): | Not tested |
| *Golovinomyces cichoracearum* (Gc; ex Ec)): | Not tested |
| *Pseudoperonospora cubensis* (Pcu): | Not tested |
| *Podosphaera xanthii* (Px; ex Sf): | Resistant (IR) |

TABLE 2

Differences in physiological and morphological characteristics of 19-720 RZ with closest known variety Quarto RZ F1.

| Characteristic | 19-720 RZ | Quarto RZ F1 |
|---|---|---|
| Fruit: intensity of ground color of skin | Dark to very dark | medium |
| Leaf: size | Very small | small |
| Fruit: weight | 30-40 g | 40-50 g |
| Fruit: length | Very short to short | short |
| Stem: intensity of green color | Dark | medium |

In an embodiment, the invention relates to a cucumber plant that has all the morphological and physiological characteristics of the invention and has acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits may be introduced into a hybrid by backcrossing the trait into one or both parents, useful traits may be introduced directly into the plant of the invention, being a plant of hybrid cucumber variety 19-720 RZ, by genetic transformation techniques; and, such plants of hybrid cucumber variety 19-720 RZ that have additional genetic information introduced into the genome or that express additional traits by having the DNA coding therefore introduced into the genome via transformation techniques, are within the ambit of the invention, as well as uses of such plants, and the making of such plants.

Genetic transformation may therefore be used to insert a selected transgene into the plant of the invention, being a plant of hybrid cucumber variety 19-720 RZ or may, alternatively, be used for the preparation of transgenes which may be introduced by backcrossing. Methods for the transformation of plants, including cucumber, are well known to those of skill in the art.

Vectors used for the transformation of cucumber cells are not limited so long as the vector may express an inserted DNA in the cells. For example, vectors which may comprise promoters for constitutive gene expression in cucumber cells (e.g., cauliflower mosaic virus 35S promoter) and promoters inducible by exogenous stimuli may be used. Examples of suitable vectors include pBI binary vector. The "cucumber cell" into which the vector is to be introduced includes various forms of cucumber cells, such as cultured cell suspensions, protoplasts, leaf sections, and callus. A vector may be introduced into cucumber cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which may be used to propel particles coated with DNA or cells through a screen, such as a stainless steel or Nytex screen, onto a surface covered with target cucumber cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of cucumber variety 19-720 RZ.

*Agrobacterium*-mediated transfer is another widely applicable system for introducing gene loci into plant cells. An advantage of the technique is that DNA may be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes may be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including cucumber plant cells, is well known in the art (See, e.g., U.S. Pats. No. 7,250,560 and 5,563,055).

Transformation of plant protoplasts also may be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for cucumber plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, the promoter for the thylakoid membrane proteins from spinach (psaD, psaF, psaE, PC, FNR, atpC, atpD, cab, rbcS) (see U.S. Pat. No. 7,161,061), the CAB-1 promoter from spinach (see U.S. Pat. No. 7,663,027), the promoter from maize prolamin seed storage protein (see U.S. Pat No. 7,119,255), and other plant DNA virus promoters known to express in plant cells. A variety of plant gene promoters that are regulated in response to environmental, hormonal, chemical, and/or developmental signals may be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wun1, or (5) chemicals such as methyl jasmonate, salicylic acid, or Safener. It may also be advantageous to employ organ-specific promoters.

Exemplary nucleic acids which may be introduced to the cucumber variety of this invention include, for example, DNA sequences or genes from another species, or even genes or sequences which originate from or are present in cucumber species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA may include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of cucumber variety 19-720 RZ. Non-limiting examples of particular genes and corresponding phenotypes one may choose to introduce into a cucumber plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences may affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat No. 7,576,262, "Modified gene-silencing RNA and uses thereof.")

U.S. Pats. Nos. 7,122,720, 7,081,363, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed cucumber and/or methods of transforming cucumber or cucumber plant cells, and techniques from these US Patents, as well as promoters, vectors, etc., may be employed in the practice of this invention to introduce exogenous nucleic acid sequence(s) into a plant of cucumber variety 19-720 RZ (or cells thereof), and exemplify some exogenous nucleic acid sequence(s) which may be introduced into a plant of cucumber variety 19-720 RZ (or cells thereof) of the invention, as well as techniques, promoters, vectors etc., to thereby obtain further plants of cucumber variety 19-720 RZ, plant parts and cells, seeds, other propagation material, harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture may be derived from leaves, pollen, embryos, cotyledon, hypocotyls, meristematic cells, roots, root tips, anthers, flowers, seeds and stems. Tissue culture methodologies relating to *Cucumis sativus* plants are well known in the art (e.g. Handley, L. W., and O. L. Chambliss. In vitro propagation of *Cucumis sativus* L. HortScience 14: 22-23 (1979); J. F. Reynolds. 14. In vitro culture of vegetable crops. Chapter 12.2 Cucumber In: I. K. Vasil: Plant Cell and Tissue Culture: 351-354 (1994)).

Also, the invention comprehends methods for producing a seed of a 19-720 RZ-derived cucumber plant which may comprise (a) crossing a plant of cucumber variety 19-720 RZ, representative seed of which having been deposited under NCIMB Accession No. NCIMB 42966, with itself or a second cucumber plant, and (b) whereby seed of a 19-720 RZ-derived cucumber plant form (e.g., by allowing the plant from the cross to grow to produce seed). Such a method may further comprise (c) crossing a plant grown from 19-720 RZ-derived cucumber seed with itself or with a second cucumber plant to yield additional 19-720 RZ-derived cucumber seed, (d) growing the additional 19-720 RZ-derived cucumber seed of step (c) to yield additional 19-720 RZ-derived cucumber plants, and (e) repeating the crossing and growing of steps (c) and (d) for an additional 3-10 generations to further generate 19-720 RZ-derived cucumber plants. The invention also encompasses a 19-720-derived cucumber plant or seed produced by such method.

Backcrossing one of the parents of a hybrid may also be used to improve an inbred plant. Backcrossing transfers a specific desirable trait from one inbred or non-inbred source to an inbred that lacks that trait. This may be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention also encompasses a method of introducing a desired trait into a plant of hybrid cucumber variety 19-720 RZ which may comprise: (a) crossing a parent plant of hybrid cucumber variety 19-720 RZ, with a second cucumber plant that may comprise the desired trait to produce F1 progeny; (b) selecting an F1 progeny that may comprise the desired trait; (c) crossing the selected F1 progeny with said parent plant of cucumber variety 19-720 RZ, to produce backcross progeny and (d) selecting backcross progeny which may comprise the desired trait and the physiological and morphological characteristics of said parent plant of cucumber variety 19-720 RZ, when grown in the same environmental conditions.

The aforementioned method of introducing a desired trait into a plant of hybrid cucumber variety 19-720 RZ could also further comprise (e) repeating steps (c) and (d) one or more times in succession to produce selected fourth or higher backcross progeny that may comprise the desired trait and the physiological and morphological characteristics of said parent plant of cucumber variety 19-720 RZ and (h) crossing the backcrossed parent plant having the added desired trait with the other parent plant to obtain a plant which may comprise the desired trait and all of the physiological and morphological characteristics of a plant of cucumber variety 19-720 RZ.

The invention additionally provides a method of introducing a desired trait into a plant of hybrid cucumber variety 19-720 RZ by reverse breeding (See generally allowed U.S. application Ser. No. 10/487,468, published as 2006-0179498 A1), which may comprise the following steps: (a) allowing the hybrid cucumber plant to produce haploid cells, while suppressing recombination, (b) growing haploid cells into diploid plants, (c) selecting those homozygous plants which together constitute the hybrid variety of the invention as parent plants for the said hybrid, (d) crossing one of the said parent plants with a plant having the desired trait, (e) crossing the selected F1 progeny with said parent plant, to produce backcross progeny; (f) selecting backcross progeny which may comprise the desired trait and the physiological and morphological characteristic of the parent plant; and, optionally, (g) repeating steps (e) and (f) one or more times in succession to produce selected fourth or higher backcross progeny that may comprise the desired trait and all of the physiological and morphological characteristics of said parent plant, (h) crossing the backcrossed parent plant having the added desired trait with the other parent plant obtained after reverse breeding to obtain a plant which may comprise the desired trait and all of the physiological and morphological characteristics of a plant of cucumber variety 19-720 RZ.

The invention further involves a method of determining the genotype of a plant of cucumber variety 19-720 RZ, representative seed of which has been deposited under NCIMB Accession No. NCIMB 42966, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples. This method may additionally comprise the step of storing the results of detecting the plurality of polymorphisms on a computer readable medium, or transmitting the results of detecting the plurality of polymorphisms. The plurality of polymorphisms are indicative of and/or give rise to the expression of the morphological and physiological characteristics of cucumber variety 19-720 RZ.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that may store computer searchable information.

As used herein, a "computer readable medium" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan may readily appreciate how any of the presently known computer readable mediums may be used to create a manufacture which may comprise computer readable medium having recorded thereon a polymorphism of the present invention.

As used herein, "recorded" refers to the result of a process for storing information in a retrievable database or computer readable medium. For instance, a skilled artisan may readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on a computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan may readily appreciate that any one of the currently available computer-based system are suitable for use in the present invention.

The invention is further described by the following numbered paragraphs:

1. A cucumber (*Cucumis sativus*) plant designated 19-720 RZ, representative seed of which having been deposited under NCIMB Accession No. 42966.

2. The plant of paragraph 1, which is grown from seed having been deposited under NCIMB Accession No. 42966.

3. A seed of the plant of paragraph 1.

4. A seed that is capable of growing into the plant of paragraph 1.

5. A part of the plant of paragraph 1, wherein said part of the plant is suitable for sexual reproduction.

6. A part of the plant of paragraph 5, wherein said part comprises a microspore, pollen, an ovary, an ovule, an embryo sac, or an egg cell.

7. A part of the plant of paragraph 1, wherein said part of the plant is suitable for vegetative reproduction.

8. A part of paragraph 7, said part comprises a cutting, a root, a stem, a cell, or a protoplast.

9. A tissue culture of regenerable cells from the cucumber plant of paragraph 1.

10. The cell or protoplast of paragraph 8 derived from a leaf, pollen, an embryo, a cotyledon, a hypocotyl, a meristematic cell, a root, a root tip, an anther, a flower, a seed, or a stem.

11. A method for producing a progeny plant of a cucumber (*Cucumis sativus*) plant of paragraph 1, comprising crossing the plant of paragraph 1 with itself or with another *Cucumis sativus* plant, harvesting the resultant seed, and growing said seed.

12. A progeny plant of a cucumber (*Cucumis sativus*) plant of paragraph 1, wherein said progeny plant has genetic material for exhibiting the morphological and physiological characteristics as found in cucumber variety 19-720 RZ; wherein the genetic information is as contained in a plant, representative seed of which having been deposited under NCIMB Accession No. 42966.

13. A progeny of a cucumber (*Cucumis sativus*) plant of paragraph 1, having all the morphological and physiological characteristics of the cucumber (*Cucumis sativus*) plant of paragraph 1, representative seed of which having been deposited under NCIMB Accession No. 42966, wherein the morphological and physiological characteristics are as found in cucumber variety 19-720 RZ, representative seed of which having been deposited under NCIMB Accession No. 42966.

14. A progeny of a cucumber plant of paragraph 12 or paragraph 13, representative seed of which having been deposited under NCIMB Accession No. 42966, wherein the progeny is further modified in one or more other characteristics.

15. Progeny as in paragraph 14, wherein the modification is effected by mutagenesis.

16. Progeny as in paragraph 14, wherein the modification is effected by transformation with a transgene.

17. A method of producing an inbred cucumber (*Cucumis sativus*) plant derived from hybrid cucumber (*Cucumis sativus*) variety 19-720 RZ, comprising the steps:

a) preparing a progeny plant derived from hybrid cucumber (*Cucumis sativus*) variety 19-720 RZ by crossing the plant of paragraph 1 with itself or a second *Cucumis sativus* plant;

b) crossing the progeny plant with itself or a second *Cucumis sativus* plant to produce a seed of a progeny plant of a subsequent generation;

c) growing a progeny plant of a subsequent generation from said seed and crossing the progeny plant of a subsequent generation with itself or a second *Cucumis sativus* plant; and d) repeating step b) or c) for at least 3 more generations to produce an inbred *Cucumis sativus* plant derived from the hybrid cucumber (*Cucumis sativus*) variety 19-720 RZ.

18. An inbred cucumber plant produced by the method of paragraph 17.

19. A method of producing a cucumber fruit comprising: (a) obtaining a plant according to paragraph 1 or 2, wherein the plant has been cultivated to develop fruit; and (b) collecting a cucumber fruit from the plant.

20. A fruit produced by the method of paragraph 19.

21. The fruit of paragraph 20, wherein the fruit is part of a food product, optionally in processed form.

22. A method for producing a seed of a 19-720 RZ-derived cucumber plant comprising (a) crossing a plant of cucumber variety 19-720 RZ, representative seed of which having been deposited under NCIMB Accession No. NCIMB 42966, with itself or a second cucumber plant, and (b) whereby seed of a 19-720 RZ-derived cucumber plant forms.

23. The method of paragraph 22 further comprising (c) crossing a plant grown from 19-720 RZ-derived cucumber seed with itself or with a second cucumber plant to yield additional 19-720 RZ-derived cucumber seed, (d) growing the additional 19-720 RZ-derived cucumber seed of step (c) to yield additional 19-720 RZ-derived cucumber plants, and (e) repeating the crossing and growing of steps (c) and (d) for an additional 3-10 generations to generate further 19-720 RZ-derived cucumber plants.

24. A method of introducing a desired trait into a parent plant of hybrid cucumber variety 19-720 RZ comprising:

a) crossing a parent plant of hybrid cucumber variety 19-720 RZ, representative seed of which having been deposited under NCIMB Accession No. 42966 with a second *Cucumis sativus* plant that comprises the desired trait to produce F1 progeny;

(b) selecting an F1 progeny that comprises the desired trait;

(c) crossing the selected F1 progeny with said parent plant of cucumber variety 19-720 RZ, to produce backcross progeny and (d) selecting backcross progeny comprising the desired trait and the physiological and morphological characteristics of said parent plant of cucumber variety 19-720 RZ, when grown in the same environmental conditions.

25. The method of paragraph 24 further comprising: (e) repeating steps (c) and (d) one or more times in succession to produce selected fourth or higher backcross progeny that comprises the desired trait and all of the physiological and morphological characteristics of said parent plant of cucumber variety 19-720 RZ, when grown in the same environmental conditions.

26. The method of paragraph 24 wherein the parent plant is obtained by reverse breeding.

27. A method of determining the genotype of a plant of cucumber variety 19-720 RZ, representative seed of which has been deposited under NCIMB Accession No. NCIMB 42966, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms are indicative of cucumber (*Cucumis sativus*) variety 19-720 RZ and/or give rise to the expression of any one or more, or all, of the morphological and physiological characteristics of cucumber (*Cucumis sativus*) variety 19-720 RZ as described in paragraph 1.

28. The method of paragraph 27 additionally comprising the step of storing the results of detecting the plurality of polymorphisms on a computer readable medium, or transmitting the results of detecting the plurality of polymorphisms.

Having thus described in detail preferred embodiments of the present invention, it is to be understood that the invention is not to be limited to particular details set forth in the above description as many apparent variations thereof are possible without departing from the spirit or scope of the present invention.

What is claimed is:

1. A cucumber (*Cucumis sativus*) plant designated 19-720 RZ, representative seed of which having been deposited under NCIMB Accession No. 42966.

2. The plant as claimed in claim 1, which is grown from seed having been deposited under NCIMB Accession No. 42966.

3. A seed that is capable of growing into the plant of claim 1.

4. A part of the plant of claim 1,
wherein said part of the plant is suitable for vegetative reproduction,
wherein said part of the plant comprises a cutting, a root, a stem, a cell, or a protoplast,
wherein the cell or the protoplast is derived from a leaf, a cotyledon, a hypocotyl, a meristematic cell a root, a root tip, an anther, a flower, or a stem, and
wherein said part of the plant has all the same genetic material as contained in hybrid cucumber (*Cucumis sativus*) variety 19-720 RZ, representative seed of which having been deposited under NCIMB Accession No. 42966.

5. A tissue culture of regenerable cells from the cucumber plant of claim 1,
wherein the tissue culture is derived from a leaf, a cotyledon, a hypocotyl, a meristematic cell a root, a root tip, an anther, a flower or a stem, and
wherein the tissue culture has all the same genetic material as contained in hybrid cucumber (*Cucumis sativus*) variety 19-720 RZ, representative seed of which having been deposited under NCIMB Accession No. 42966.

6. A method for producing a progeny plant of a cucumber (*Cucumis sativus*) plant of claim 1, said method comprising crossing the plant of claim 1 with itself or with another *Cucumis sativus* plant,
harvesting the resultant seed, and
growing said seed.

7. A method of producing a cucumber (*Cucumis sativus*) plant derived from hybrid cucumber (*Cucumis sativus*) variety 19-720 RZ, said method comprising the steps:

a) preparing a progeny plant derived from hybrid cucumber (*Cucumis sativus*) variety 19-720 RZ by crossing the plant of claim 1 with itself or a second *Cucumis sativus* plant;

b) crossing the progeny plant with itself or the second *Cucumis sativus* plant to produce a seed of a progeny plant of a subsequent generation;

c) growing a progeny plant of a subsequent generation from said seed and crossing the progeny plant of a subsequent generation with itself or the second *Cucumis sativus* plant; and d) repeating step b) or c) for 3 more generations to produce a *Cucumis sativus* plant derived from the hybrid cucumber (*Cucumis sativus*) variety 19-720 RZ.

8. A method of producing a cucumber fruit, said method comprising:
   (a) obtaining the plant according to claim 1, wherein the plant has been cultivated to develop fruit; and
   (b) collecting a cucumber fruit from the plant.

9. A fruit produced by the method of claim 8.

10. A food product comprising the fruit of claim 9, optionally in processed form.

11. A method for producing a seed of a 19-720 RZ-derived cucumber plant, said method comprising
   (a) crossing a plant of cucumber variety 19-720 RZ, representative seed of which having been deposited under NCIMB Accession No. NCIMB 42966, with itself or a second cucumber plant, and
   (b) whereby seed of a 19-720 RZ-derived cucumber plant forms.

12. The method of claim 11 further comprising
   (c) crossing a plant grown from 19-720 RZ-derived cucumber seed with itself or with a second cucumber plant to yield additional 19-720 RZ-derived cucumber seed,
   (d) growing the additional 19-720 RZ-derived cucumber seed of step (c) to yield additional 19-720 RZ-derived cucumber plants, and
   (e) repeating the crossing and growing of steps (c) and (d) for an additional 3-10 generations to generate further 19-720 RZ-derived cucumber plants.

* * * * *

UNITED STATES PATENT AND TRADEMARK OFFICE
CERTIFICATE OF CORRECTION

PATENT NO. : 10,721,890 B2
APPLICATION NO. : 15/887070
DATED : July 28, 2020
INVENTOR(S) : René Wilhelmus Adrianus Aarts It is certified that error appears in the above-identified patent and that said Letters Patent is hereby corrected as shown below:

In the Claims

Please amend Claim 4, at Column 18, Line 36 as follows:
4. A part of the plant of claim 1, wherein said part of the plant is suitable for vegetative reproduction, wherein said part of the plant comprises a cutting, a root, a stem, a cell, or a protoplast, wherein the cell or the protoplast is derived from a leaf, a cotyledon, a hypocotyl, a meristematic cell, a root, a root tip, an anther, a flower, or a stem, and wherein said part of the plant has all the same genetic material as contained in hybrid cucumber (Cucumis sativus) variety 19-720 RZ, representative seed of which having been deposited under NCIMB Accession No. 42966.

Please amend Claim 5, at Column 18, Line 46 as follows:
5. A tissue culture of regenerable cells from the cucumber plant of claim 1, wherein the tissue culture is derived from a leaf, a cotyledon, a hypocotyl, a meristematic cell, a root, a root tip, an anther, a flower or a stem, and wherein the tissue culture has all the same genetic material as contained in hybrid cucumber (Cucumis sativus) variety 19-720 RZ, representative seed of which having been deposited under NCIMB Accession No. 42966.

Signed and Sealed this
First Day of June, 2021

Drew Hirshfeld
*Performing the Functions and Duties of the
Under Secretary of Commerce for Intellectual Property and
Director of the United States Patent and Trademark Office*